United States Patent
Gong

(10) Patent No.: US 12,397,021 B2
(45) Date of Patent: Aug. 26, 2025

(54) TRADITIONAL CHINESE MEDICINE COMPOSITION FOR TREATING CORONARY MYOCARDIAL BRIDGE AND APPLICATION THEREOF

(71) Applicant: Affiliated Hospital of Liaoning University of Traditional Chinese Medicine, Shenyang (CN)

(72) Inventor: Lihong Gong, Shenyang (CN)

(73) Assignee: Affiliated Hospital of Liaoning University of Traditional Chinese Medicine, Shenyang (CN)

( * ) Notice: Subject to any disclaimer, the term of this patent is extended or adjusted under 35 U.S.C. 154(b) by 0 days.

(21) Appl. No.: 18/980,483

(22) Filed: Dec. 13, 2024

(65) Prior Publication Data

US 2025/0222041 A1  Jul. 10, 2025

(30) Foreign Application Priority Data

Jan. 9, 2024  (CN) .......................... 202410030922.0

(51) Int. Cl.

| | | |
|---|---|---|
| A61K 36/00 | (2006.01) | |
| A61K 35/646 | (2015.01) | |
| A61K 35/648 | (2015.01) | |
| A61K 36/236 | (2006.01) | |
| A61K 36/484 | (2006.01) | |
| A61K 36/65 | (2006.01) | |
| A61K 36/66 | (2006.01) | |
| A61K 36/9066 | (2006.01) | |
| A61P 9/00 | (2006.01) | |

(52) U.S. Cl.
CPC .......... *A61K 35/646* (2013.01); *A61K 35/648* (2013.01); *A61K 36/236* (2013.01); *A61K 36/484* (2013.01); *A61K 36/65* (2013.01); *A61K 36/66* (2013.01); *A61K 36/9066* (2013.01); *A61P 9/00* (2018.01)

(58) Field of Classification Search
CPC .......................... A61K 35/648; A61K 35/646
See application file for complete search history.

(56) References Cited

FOREIGN PATENT DOCUMENTS

| CN | 1334121 | | 2/2002 |
|---|---|---|---|
| CN | 105435128 A | * | 3/2016 |
| CN | 105616540 A | * | 6/2016 |
| CN | 105920375 | | 9/2016 |
| CN | 110237211 | | 9/2019 |
| CN | 115177669 | | 10/2022 |

OTHER PUBLICATIONS

Notification to Grant Patent Right for Invention for Chinese Patent Application No. 202410030922.0, issued Jul. 1, 2024, 3 pages.
First Search Report for Chinese Patent Application No. 202410030922.0, issued Jun. 27, 2024, 5 pages.
Cai, et al., "A Study on the Rule of Chinese Medicine Prescriptions for Coronary Heart Disease Based on Data Mining," China Academic Journal Electronic Publishing House, Chinese General Practice vol. 01 S1, Jul. 2021, 3 pages.
Tingting, et al., "Analysis on Advantages of TCM Syndrome Differentiation for Myocardial Bridge," Journal of Practical Traditional Chinese Internal Medicine vol. 34 No. 3, Mar. 2020, 4 pages.
Kang, et al., "Research progress on integrated traditional Chinese and Western medicine treatment of coronary artery myocardial bridge," Journal of Emergency in Traditional Chinese Medicine, vol. 26, Issue 2, Feb. 28, 2017, 5 pages.

* cited by examiner

*Primary Examiner* — Qiuwen Mi
(74) *Attorney, Agent, or Firm* — DLA PIPER LLP (US)

(57) ABSTRACT

A traditional Chinese medicine composition for treating coronary myocardial bridge and an application thereof are provided. The traditional Chinese medicine composition includes the following components in parts by weight: 2-10 parts of scorpion, 2-10 parts of centipede, 15-50 parts of *Radix paeoniae Alba*, 5-25 parts of *Radix glycyrrhizae Preparata*, 10-30 parts of *Rhizoma chuanxiong*, 10-30 parts of *Radix curcumae* and 10-30 parts of *Rhizoma corydalis*.

11 Claims, No Drawings

TRADITIONAL CHINESE MEDICINE COMPOSITION FOR TREATING CORONARY MYOCARDIAL BRIDGE AND APPLICATION THEREOF

CROSS-REFERENCE TO RELATED APPLICATIONS

This application claims priority to Chinese Patent Application No. 202410030922.0, filed on Jan. 9, 2024, the contents of which are hereby incorporated by reference.

TECHNICAL FIELD

The present disclosure relates to the technical field of biomedicine, and in particular relates to a traditional Chinese medicine composition for treating coronary myocardial bridge and an application thereof.

BACKGROUND

Coronary myocardial bridge (abbreviated as myocardial bridge) is a common clinical coronary artery malformation, which refers to the coronary artery passing through the myocardium of the heart and compressing the coronary artery during the contraction and relaxation of myocardial fibers during the cardiac cycle, causing a decrease in coronary blood flow reserve. The myocardium covering the coronary artery is called myocardial bridge, and the compressed coronary artery is called mural coronary artery. The detection rate of myocardial bridge is influenced by the examination methods, and there are great differences. The average detection rate of coronary computed tomographic angiography (CCTA) is 3.5%-58%, and the detection rate of myocardial bridge in coronary angiography (CAG) is 3.96%-10.69%. The detection rate of women is higher than that of men, and the detection rate of patients with hypertrophic cardiomyopathy is much higher than that of the general population. More than 60% of myocardial bridges occur in the proximal and middle blood vessels of the anterior descending branch.

At present, it has been proved that the mechanism of myocardial bridge formation is related to the abnormal development position of blood vessels in embryonic period. During the cardiac cycle, both contraction and relaxation of myocardial fibers will compress blood vessels (the coronary blood flow in systolic period is only 20%-30% of that in diastolic period), causing insufficient coronary blood perfusion and inducing coronary artery spasm, leading to the dysfunction of vascular endothelium in mural coronary artery, increased plasma endothelin-1 (ET-1) level, and decreased NO level. Patients with mild myocardial bridge compression may have no symptoms, or suffer from chest tightness, pain, palpitation and shortness of breath, and other symptoms after fatigue and emotional excitement. Severe compression may cause acute coronary syndrome, malignant arrhythmia, cardiogenic shock and even sudden death.

With the development of medical technology and the popularization of medical examination equipment, the detection rate of myocardial bridge has increased year by year, and the population base in China is huge, and the number of myocardial bridge detection has increased significantly every year. The consensus of experts in China suggests that for patients with myocardial bridge and clear evidence of myocardial ischemia, drug treatment (ß-blockers and non-dihydropyridine calcium antagonists) should be given priority, and by controlling heart rate and reducing myocardial contractility, the systolic coronary artery compression may be reduced, the diastolic filling time may be prolonged, the coronary blood perfusion may be increased, the coronary spasm may be relieved, and the myocardial blood supply may be improved. The application of nitrate drugs to increase sympathetic nerve excitability should be avoided. When the drug treatment is poor, the symptoms occur frequently, and the Canadian Cardiovascular Society (CCS) grade of angina pectoris is above grade 3, it is suggested to perform supra-arterial myotomy or coronary artery bypass grafting (CABG). However, the latest research abroad shows that although the objective evidence of myocardial ischemia disappeared after myocardial bridge release, some patients still failed to improve their chest pain symptoms. CABG may improve the blood supply to the distal myocardium, but the most common postoperative complication is bridging occlusion caused by competitive blood flow. On the whole, among the current treatment methods for coronary myocardial bridge, drug treatment has obvious limitations, and it often has poor curative effect, high surgical difficulty, high risk, high cost, poor postoperative prognosis, lack of long-term follow-up research under a large number of samples, and western medicine treatment has fallen into a bottleneck.

Although there is no record of the name of myocardial bridge disease in traditional Chinese medicine, it may be classified into the category of "chest obstruction and heartache" according to its symptoms such as chest tightness, chest pain, shortness of breath and palpitation. According to the characteristics of chest stuffiness and heartache, "weak pulse at yang and stringy pulse at yin", combined with clinical experience, modern physicians summarize the pathogenesis of myocardial bridge in traditional Chinese medicine as follows: liver fails to relieve stagnation, and flow of vital energy and blood circulation is not smooth. Soothing the liver and relieving depression, promoting circulation of the flow of vital energy and relieving pain are mostly used as treatment methods. Although some curative effects have been achieved, the clinical application is limited. For elderly patients with chronic illnesses or vital energy and blood deficiency, liver yin is often depleted, vital energy and blood are damaged, and other visceral diseases are aggravated. Therefore, the treatment methods may not be widely and long-term applied to the treatment of myocardial bridge. Therefore, it is necessary to develop a new traditional Chinese medicine composition for treating coronary myocardial bridge, which is more suitable for clinical application.

SUMMARY

An objective of the present disclosure is to provide a traditional Chinese medicine composition for treating coronary myocardial bridge and an application thereof, so as to solve the problems existing in the prior art. The traditional Chinese medicine composition may not only loosen coronary myocardial bridge, improve coronary blood supply, relieve coronary spasm, but also reduce blood lipid level, prevent and treat coronary atherosclerosis, relieve patients' anxiety, improve patients' quality of life, and reduce the occurrence of cardiovascular adverse events, with remarkable clinical efficacy.

To achieve the above objectives, the present disclosure provides the following scheme:

The present disclosure provides a traditional Chinese medicine composition for treating coronary myocardial bridge, including following components in parts by weight:

2-10 parts of scorpion, 2-10 parts of centipede, 15-50 parts of *Radix paeoniae Alba*, 5-25 parts of *Radix glycyrrhizae Preparata*, 10-30 parts of *Rhizoma chuanxiong*, 10-30 parts of *Radix curcumae* and 10-30 parts of *Rhizoma corydalis*.

Optionally, the traditional Chinese medicine composition includes following components in parts by weight: 3 parts of scorpion, 2 parts of centipede, 30 parts of *Radix paeoniae Alba*, 10 parts of *Radix glycyrrhizae Preparata*, 15 parts of *Rhizoma chuanxiong*, 15 parts of *Radix curcumae* and 15 parts of *Rhizoma corydalis*.

The present disclosure also provides an application of the traditional Chinese medicine composition in preparing medicines for treating coronary myocardial bridge.

In an embodiment, treating coronary myocardial bridge refers to relieving chest pain and/or palpitation symptoms caused by coronary myocardial bridge, improving the quality of daily life and improving heart function.

The present disclosure also provides a medicine for treating coronary myocardial bridge, and raw materials include the traditional Chinese medicine composition.

In an embodiment, the medicine also includes pharmaceutically acceptable excipients.

In an embodiment, the carrier includes an emulsifier, a filler, a binder, a disintegrant, a colorant and/or a cosolvent.

In an embodiment, a dosage form of the medicine is an oral dosage form.

In an embodiment, the oral dosage form includes decoction, granule, capsule, pill, tablet or ointment.

The present disclosure also provides a preparation method of the medicine, including steps of extracting active ingredients in the traditional Chinese medicine composition by using a solvent, and then adding pharmaceutically acceptable excipients to prepare the medicine.

*Radix paeoniae Alba* is the dried root of *Paeonia lactiflora* Pall. of Ranunculaceae, which is sour and bitter in flavor, slightly cold in nature, and belongs to the liver and spleen meridians, and has the functions of calming the liver and relieving pain, nourishing blood and regulating menstruation, astringing yin and arresting sweating. Modern pharmacological research shows that main ingredients of *Radix paeoniae Alba* are paeoniflorin, volatile oil of *Paeonia lactiflora* Pall., triterpenoids and other substances. The extract of *Paeonia lactiflora* Pall. has the effects of protecting liver from injury, reducing degeneration and necrosis of hepatocytes, anti-ulcer, relieving smooth muscle spasm, anti-thrombosis, reducing blood viscosity, increasing plasma NO level, reducing Endothelin (ET) level, as well as anti-inflammatory and analgesic effects.

*Radix glycyrrhizae Preparata* is a dried root or rhizome of *Glycyrrhiza uralensis* Fisch. of Leguminosae or *G. inflata* Bata. and *G. glabra* L. of the same genus, which is sweet in flavor, neutral in nature, belongs to the heart, lung, spleen and stomach meridians, and has the functions of benefiting vital energy, invigorating middle warmer, eliminating phlegm, relieving cough, and detoxicating. Modern pharmacological research shows that main ingredients of *Radix glycyrrhizae Preparata* are glycyrrhizic acid, glycyrrhetinic acid, liquiritin, $FM_{100}$, licorice flavonoids and other substances, where flavonoids such as isoliquiritigenin and $FM_{100}$ have obvious spasmolytic effects. The extract of *Radix glycyrrhizae Preparata* may slow down the heart rate and prolong the P-R and Q-T intervals in anesthetized rats. Glycyrrhizin may also reduce the levels of plasma cholesterol and triglyceride in rabbits.

Scorpion, a dried whole worm of *Buthus martensii* Karsch, is salty, pungent, neutral in nature, toxic, and belongs to the liver meridian, and has the functions of calming rheumatic pains, relieving spasm, dredging collaterals, relieving pain, detoxicating and resolving hard mass. Modern pharmacological research shows that main ingredients of scorpion are scorpion venom, various amines and amino acids, cholesterol, phosphatidylcholine and various fatty acids. Scorpion extract has inhibitory effect on thrombosis of inferior vena cava in rats and may prolong coagulation time and prothrombin time. Low dose scorpion venom may slow down the heart rate through autonomic nerve regulation, while high dose scorpion venom may enhance myocardial contractility and cause blood pressure to rise. Scorpion venom ingredients in scorpion body and scorpion tail preparations have strong analgesic effects on visceral pain, trigeminal neuralgia, skin burning pain and other pains.

Centipede, the dried body of *Scolopendra subspinipes mutilans* L. koch, is pungent in flavor, warm in nature, toxic, and enters the liver meridian, and has the effects of calming rheumatic pains and stopping spasm, attacking toxin and resolving hard mass, dredging collaterals and relieving pain. Modern pharmacological research shows that main ingredients of centipede are a variety of unsaturated fatty acids and trace elements. Centipede water extract has an analgesic percentage of 53% in mice, a 50% increase in pain threshold for more than 4 hours, and anti-inflammatory, vasodilatory, and antihypertensive effects. When used in high doses, centipede water extract has the effect of enhancing myocardial contractility.

*Rhizoma chuanxiong*, the rhizome of Ligusticun Chuanxiong Hort, an Umbelliferae plant, is pungent in flavor and warm in nature, and belongs to liver, gallbladder and pericardium meridians, and has the effects of promoting blood circulation and circulation of the flow of vital energy, relieving rheumatic pains and relieving pain. Modern pharmacological research shows that its main ingredients are ligustrazine and ferulic acid, and *Rhizoma chuanxiong* decoction may significantly increase the amplitude of cardiac contraction and slow down the heart rate in experiments on isolated toad and frog hearts. In the experimental study of ligustrazine, it is found that ligustrazine has relaxing effect on a variety of isolated blood vessels, may antagonize the vasoconstriction caused by norepinephrine, prostaglandin F2Q, high concentration KCL, endothelin-1, $CaCl_2$, etc., reduce the expression of various inflammatory factors such as monocyte chemoattractant protein-1 (MCP-1) and intercellular cell adhesion molecule-1 (ICAM-1) in plasma, improve the environment of vascular endothelial cells, and has a protective effect against ischemia-reperfusion injury in multiple organs such as the heart, lungs, brain, liver, and kidneys.

*Radix curcumae*, is a dry root tuber of *Curcuma aromatica* Salisb., a perennial herb of Zingiberaceae, with pungent and bitter flavor and cold nature, which belongs to liver and lung meridians, and has the effects of clearing away heart-fire, relieving depression, promoting circulation of the flow of vital energy, promoting blood circulation, removing blood stasis, promoting gallbladder function and eliminating jaundice. Modern pharmacological studies have found that the main ingredient of *Radix curcumae* is curcumin, and the main ingredients of the volatile oil of curcumin are sesquiterpene, sesquiterpene enol, camphor and so on. The efficacy of *Radix curcumae* in clearing away heart-fire and relieving depression is mainly reflected in its anti-myocardial ischemia, antithrombotic and hypolipidemic effects, and the water extract and ethanol extract of *Radix curcumae* also have good analgesic effects.

*Rhizoma corydalis*, a dried tuber of Corydalis W. T. WANG, is pungent, bitter and warm in nature, and belongs to liver, spleen and heart meridians. It is called "medicine for vital energy in blood" and has the functions of regulating the flow of vital energy, relieving pain, promoting blood circulation and removing blood stasis. Modern pharmacological research shows that its main ingredients are tetrahydropalmatine, corydaline, corydalis L and dehydrocorydaline, where tetrahydropalmatine has the strongest analgesic effect. In the study of *Rhizoma corydalis*, it was found that the analgesic effect of *Rhizoma corydalis* reaches its peak in half an hour and may last for more than 2 hours. Compared with the total morphine base, the analgesic potency of *Rhizoma corydalis* is about 40% of that of morphine, and there is no addiction and withdrawal reaction. *Rhizoma corydalis* has a more significant effect on cardiovascular system. *Rhizoma corydalis* may increase coronary blood flow and myocardial nutrient blood flow, dilate peripheral blood vessels, lower blood pressure and protect necrotic myocardial cells. In the further study, it was found that tetrahydropalmatine and other substances may competitively antagonize the arterial contraction caused by norepinephrine by inhibiting the release of intracellular $Ca^{2+}$.

The "pharmaceutically acceptable" ingredients in the present disclosure are ingredients that are suitable for humans and/or animals and have no excessive adverse side effects (e.g., toxicity, irritation, etc.), that is, substances with reasonable benefit-risk ratio.

The "pharmaceutically acceptable excipients" in the present disclosure refer to the general name of all additional materials except the main drug in pharmaceutical preparations, including various excipients, diluents, etc. The excipient itself does not have to have relevant drug activity, but it is not excessively toxic after application. The specific excipients are well known to ordinary technicians in this field. The specific form may be liquid or solid. The excipients may have some auxiliary functions, such as emulsifier, filler, adhesive, disintegrant, colorant, cosolvent and so on.

The present disclosure discloses the following technical effects.

The traditional Chinese medicine composition according to the present disclosure consists of seven common traditional Chinese medicines, namely *Radix paeoniae Alba, Radix glycyrrhizae Preparata*, centipede, scorpion, *Rhizoma chuanxiong, Radix curcumae* and *Rhizoma corydalis*, and most of the medicines used belong to heart and liver meridians, and their nature is neutral and flavor is pungent. Traditional Chinese medicine believes that the liver belongs to an organ of wood, which is responsible for conducting and dispersing, regulating movement of vital energy. The heart belongs to an organ of fire, governs the blood vessels, and calms the mind. The coronary artery is compressed by the myocardial bridge, and often fails to release due to liver failure catharsis, thus affecting the coronary blood supply, leading to coronary spasm attacks and impaired cardiac function. At the same time, patients with myocardial bridge are affected by chest tightness, chest pain, palpitations and other symptoms, and often feel nervous and anxious, which aggravates liver depression and vital energy stagnation. The traditional Chinese medicine composition according to the present disclosure treats liver and heart simultaneously, regulates vital energy and blood, not only loosens the myocardial bridge that oppresses coronary vessels, but also relieves patients' tension and anxiety.

In this invention, *Radix paeoniae Alba* and *Radix glycyrrhizae Preparata* are both principal drugs, which constitute the classic prescription "Peony and Licorice Decoction" in *Treatise on Febrile Diseases*. The original text of *Treatise on Febrile Diseases* records: "If the patient has recovered and their feet are warm, Peony and Licorice Decoction should be given, and their feet will stretch out". Peony and Licorice Decoction plays a therapeutic role in the treatment of contracture and stiffness of limbs. Later generations of physicians explained the classics and gave full play to the clinical symptoms, and summarized the medication mechanism of Peony and Licorice Decoction as follows: sweet and sour, nourishing yin and blood, and is flexibly applied to the treatment of limb spasm and visceral pain. It is described in *Collection of Medical Prescriptions*: "*Radix paeoniae Alba* is sour to astringe and bitter to decline diarrhea, and may nourish vital energy; *Radix glycyrrhizae Preparata* is warm for dissipation, and is sweet for relaxing and may harmonize with the adverse qi", which is in line with the characteristics of myocardial bridge. Nourishing qi may make blood flow smoothly, and descending the adverse qi may loosen muscles. Based on this principle, Peony and Licorice Decoction is used to treat the pain and throbbing caused by coronary myocardial bridge. The traditional Chinese medicine according to the present disclosure is composed of two types of insect medicines: scorpion and centipede, and the scorpion and centipede pair medicine is called "Huiming Powder" in *New Book of Pediatrics* and also called "antispasmodic powder" in *Internal Medicine of Traditional Chinese Medicine*. It is recorded in the *Records of Tradition Chinese and Western Medicine in Combination* that "centipedes, with the fastest power of movement, may unblock the internal organs and external meridians, wherever vital energy and blood are condensed", and "Scorpions are good at entering the liver meridian . . . treating convulsions and epilepsy . . . although their nature is toxic, they turn to good and detoxify, and they are the combination medication of centipedes, and their strengths complement each other". Scorpion and centipede are a combination of two medicines, which has strong specialization and ability, quickly unblocking collaterals, calming rheumatic pains and stopping spasm, attacking poison and relieving pain. Small dose application has strong effects of slowing coronary spasm, relieving pain and anticoagulation. *Radix curcumae, Rhizoma corydalis* and *Rhizoma chuanxiong* jointly serve as adjuvants of the traditional Chinese medicine composition, except that they all have the effects of promoting circulation of the flow of vital energy, relieving depression, promoting blood circulation and removing blood stasis, and play the role of "dredging without pain" from the two aspects of vital energy and blood, and besides, *Radix curcumae* calms the nerves, clears the heart, *Rhizoma corydalis* relieves turbidity and reduces blood fat, and *Rhizoma chuanxiong* relaxes chest to relieve annoyance, so that the traditional Chinese medicine composition according to the present disclosure has the functions of reducing blood fat, preventing and treating coronary atherosclerosis, relieving patients' anxiety and improving the blood supply function of the heart, further reducing various adverse events caused by coronary spasm of myocardial bridge, and greatly improving the prognosis of myocardial bridge of coronary artery.

Based on the anatomical characteristics of coronary myocardial bridge and the pathological basis of traditional Chinese medicine, the traditional Chinese medicine composition according to the present disclosure puts forward the treatment method of "relaxing the heart and relieving spasm, dredging collaterals and relieving pain", which gives consideration to the nature and taste, meridian tropism, strict compatibility, proper priority and secondary, simultaneous regulation of vital energy and blood, simultaneous treatment of heart and liver, and gives consideration to "exorcising evil spirits without damaging the right, tonifying deficiency and not leaving stagnation", fully embodying the advantages of multi-dimensional and multi-target treatment of traditional Chinese medicine. The traditional Chinese medicine composition may not only loosen coronary myocardial bridge, improve coronary blood supply and relieve coronary spasm, but also reduce blood lipid level, prevent and treat coronary atherosclerosis, relieve patients' anxiety, improve patients' quality of life and reduce the occurrence of cardiovascular adverse events. The traditional Chinese medicine composition has obvious clinical efficacy, no obvious toxic side effects and adverse reactions, which not only solves clinical problems, but also broadens the current treatment methods of myocardial bridge, which is conducive to promoting the vigorous development of traditional Chinese medicine and has great social value.

DETAILED DESCRIPTION OF THE EMBODIMENTS

A number of exemplary embodiments of the present disclosure will now be described in detail, and this detailed description should not be considered as a limitation of the present disclosure, but should be understood as a more detailed description of certain aspects, characteristics and embodiments of the present disclosure.

It should be understood that the terminology described in the present disclosure is only for describing specific embodiments and is not used for limiting the present disclosure. In addition, for the numerical range in the present disclosure, it should be understood that each intermediate value between the upper limit and the lower limit of the range is also specifically disclosed. Intermediate values within any stated value or stated range, as well as each smaller range between any other stated value or intermediate values within the stated range are also included in the present disclosure. The upper and lower limits of these smaller ranges may be independently included or excluded from the range.

Unless otherwise specified, all technical and scientific terms used herein have the same meaning as commonly understood by one of ordinary skill in the art to which this invention relates. Although the present disclosure only describes the preferred methods and materials, any methods and materials similar or equivalent to those described herein may also be used in the practice or testing of the present disclosure. All documents mentioned in this specification are incorporated by reference to disclose and describe methods and/or materials related to the documents. In case of conflict with any incorporated document, the contents of this specification shall prevail.

It is obvious to those skilled in the art that many improvements and changes may be made to the specific embodiments of the present disclosure without departing from the scope or spirit of the present disclosure. Other embodiments will be apparent to the skilled person from the description of the present disclosure. The description and embodiments of the present disclosure are exemplary only.

The terms "including", "comprising", "having" and "containing" used herein are all open terms, which means including but not limited to.

In the preparation method of the dosage form of the traditional Chinese medicine composition in the following embodiments, the decoction is prepared by washing the weighed raw materials and adding water for cooking; the granule is prepared by weighing raw materials respectively, cleaning and cooking, filtering and combining filtrates, concentrating the filtrates, cooling, adding ethanol, mixing uniformly, standing, weighing supernatant, filtering, distilling the filtrate to remove ethanol, standing and concentrating to obtain extract, and drying and pulverizing the extract to obtain granules; the capsule is prepared by adding excipients after the extract is prepared according to the method of preparing the granule, drying, pulverizing and granulating, and filling into the capsule. Other existing dosage forms, such as pills, tablets, decoctions, etc., may be prepared according to conventional preparation methods, and will not be repeated here.

Embodiment 1

This embodiment provides a decoction prepared from the following raw materials:

30 grams (g) of *Radix paeoniae Alba*, 6 g of *Radix glycyrrhizae Preparata*, 3 g of scorpion, 2 g of centipede, 15 g of *Rhizoma chuanxiong*, 15 g of *Radix curcumae* and 15 g of *Rhizoma corydalis*.

Embodiment 2

This embodiment provides a decoction prepared from the following raw materials:

15 g of *Radix paeoniae Alba*, 15 g of *Radix glycyrrhizae Preparata*, 3 g of scorpion, 2 g of centipede, 15 g of *Rhizoma Chuanxiong*, 15 g of *Radix curcumae* and 15 g of *Rhizoma corydalis*.

Embodiment 3

This embodiment provides a decoction prepared from the following raw materials:

20 g of *Radix paeoniae Alba*, 10 g of *Radix glycyrrhizae Preparata*, 5 g of scorpion, 5 g of centipede, 15 g of *Rhizoma chuanxiong*, 15 g of *Radix curcumae* and 15 g of *Rhizoma corydalis*.

Embodiment 4

This embodiment provides a granule prepared from the following raw materials:

50 g of *Radix paeoniae Alba*, 5 g of *Radix glycyrrhizae Preparata*, 2 g of scorpion, 10 g of centipede, 10 g of *Rhizoma chuanxiong*, 10 g of *Radix curcumae* and 10 g of *Rhizoma corydalis*.

Embodiment 5

This embodiment provides a capsule prepared from the following raw materials:

30 g of *Radix paeoniae Alba*, 25 g of *Radix glycyrrhizae Preparata*, 10 g of scorpion, 5 g of centipede, 30 g of *Rhizoma chuanxiong*, 30 g of *Radix curcumae* and 30 g of *Rhizoma corydalis*.

Effect Verification:

According to the observation of clinical cases, the clinical efficacy of the traditional Chinese medicine composition according to the present disclosure in treating coronary myocardial bridge is verified by taking the frequency and duration of angina pectoris attack, ST-T segment change of electrocardiogram, left ventricular ejection fraction (LVEF) and quality of life index integral as observation indexes.

1. Materials and Methods

1.1 General Information

The subjects were 180 cases of myocardial bridge diagnosed and treated in the Affiliated Hospital of Liaoning University of Traditional Chinese Medicine from March 2016 to March 2023, which met the inclusion and exclusion criteria.

1.2 Diagnostic Criteria

Diagnostic criteria of western medicine: with reference to *Diagnosis and Treatment of Coronary Myocardial Bridge* edited by ZHANG Zhishou in 2020: during the hospital, the patient was found to have a coronary artery with different degrees of stenosis at more than two projection angles, and the blood supply of the coronary artery returned to normal at the end of diastole, that is, the "milking effect", which may be diagnosed as coronary myocardial bridge, and the Noble grade of coronary myocardial bridge is grade II-III.

Noble grade of coronary myocardial bridge: grade I, the severity of systolic compression of mural coronary artery is less than 50%, and there is no clinical manifestation; grade II, the severity of systolic compression of mural coronary artery is 50%-75%, with increased lactate and regional myocardial ischemia; grade III, the severity of systolic compression of mural coronary artery is more than 75%, with a significant increase in lactate and myocardial ischemia on electrocardiogram, and the appearance of clinical symptoms.

Diagnostic criteria of traditional Chinese medicine: with reference to the diagnostic criteria of "chest obstruction and heartache" in *Internal Medicine of Traditional Chinese Medicine* published by China Traditional Chinese Medicine Publishing House in 2021.

1.3 Inclusion Criteria

① Meeting the diagnostic criteria of coronary myocardial bridge in western medicine and the myocardial bridge grade is grade II-III.

② Meeting the diagnostic criteria of chest obstruction and heartache in traditional Chinese medicine.

1.4 Exclusion Criteria

① Not meeting the diagnostic criteria of western medicine and traditional Chinese medicine at the same time.

② There are serious life-threatening diseases such as heart, liver, kidney, hematopoietic system diseases or malignant tumors.

③ Patients with multiple coronary artery lesions or single coronary artery stenosis exceeding 70%.

④ Patients with heart rate <60 beats per minute (beats/min), blood pressure <100/70 millimeter of mercury (mmHg) or with atrioventricular block and sick sinus syndrome;

⑤ People who are allergic to known ingredients of the medication.

1.5 Suspension Criteria

① Abnormal safety indexes such as liver function, kidney function and coagulation function occurred during the treatment.

② Acute diseases such as acute myocardial infarction, severe arrhythmia and cardiogenic shock occurred during the treatment.

③ Special physiological conditions or unexpected events occurred during the research.

1.6 Research Methods

1.6.1 Treatment Method 180 cases meeting the inclusion and exclusion criteria were randomly divided into three groups of group A, group B and group C, with 60 cases in each group. The general data of the three groups were comparable (P>0.05).

Group A: The decoction of Chinese medicinal composition prepared in Embodiment 1 was taken orally, with the dosage of 100 millilitre each time (mL/time), once in the morning, once in the afternoon and once in the evening every day, 30 minutes after meals, and 8 weeks was a course of treatment.

Group B: The decoction of Chinese medicinal composition prepared in Embodiment 2 was taken orally, with the dosage of 100 mL/time, once in the morning, once in the afternoon and once in the evening every day, 30 minutes after meals, and 8 weeks was a course of treatment.

Group C: Diltiazem hydrochloride sustained-release capsules 90 mg were taken orally once a day for 8 weeks as a course of treatment.

During the treatment, blood pressure and heart rate were monitored, and oral nitrates (nitroglycerin tablets, isosorbide dinitrate tablets, etc.) were prohibited, and irritating drinks such as spirits, coffee and strong tea were avoided, spicy, greasy and cold foods were avoided, and strenuous exercise was avoided. Patients with other basic diseases continued to take conventional western medicine orally.

Observation Indexes

① The frequency and duration of angina pectoris attacks and the improvement of ST-T segment on electrocardiogram: ② left ventricular ejection fraction (LVEF); ③ quality of life index integral (SF-12).

The evaluation criteria for the efficacy of the frequency and duration of angina pectoris attacks and ST-T segment changes on electrocardiogram: marked effect: angina pectoris symptoms basically improved, and ST-T segment on electrocardiogram returned to normal or almost normal; effective: the frequency and duration of angina pectoris attacks were obviously reduced, the ST-T segment on electrocardiogram rebounded by ≥0.05 millivolt (mV) or the inverted T wave became shallower by ≥25%, or the T wave changed from flat to upright, and the conduction block was improved; ineffective: the symptoms of angina pectoris have not improved significantly, and the ST-T segment on electrocardiogram has not changed.

1.6.3 Safety Evaluation

After 8 weeks of treatment, the functions of liver, kidney and blood coagulation, routine blood, urine and stool were detected.

1.6.4 Statistical Method

SPSS26.0 statistical software was used to analyze the data. The measurement data were expressed by "mean±standard deviation" ($\bar{x}\pm s$), and the paired t test was used for comparison before and after treatment in the group, and the independent sample t test was used for comparison before and after treatment in the group; rank sum test was used to compare grade data; chi-square test was used for counting data, with P<0.05 as statistical difference and P<0.01 as significant difference.

2. Results

2.1 Improvement of Frequency and Duration of Angina Pectoris Attacks

After treatment, the frequency and duration of angina pectoris attacks in three groups were improved (P<0.05), especially in group A (P<0.01), and the specific results are shown in Table 1.

TABLE 1

Comparison of frequency and duration of angina pectoris attacks
before and after treatment ($\bar{x} \pm s$)

| Group | Case | Number of angina attacks (times/day) | | Duration of angina pectoris (min/day) | |
|---|---|---|---|---|---|
| | | Before treatment | After treatment | Before treatment | After treatment |
| Group A | 59 | 26.34 ± 4.35 | 4.28 ± 2.30# | 86.72 ± 10.59 | 16.43 ± 3.92# |
| Group B | 59 | 25.72 ± 2.53 | 8.13 ± 3.34# | 88.50 ± 8.61 | 23.95 ± 4.19* |
| Group C | 58 | 25.96 ± 1.19 | 11.64 ± 4.68* | 87.04 ± 8.27 | 39.37 ± 4.37* |

Note:
Compared with before treatment, *P < 0.05, and compared with before treatment #P < 0.01.

2.2 Evaluation of Curative Effect of Angina Pectoris

After treatment, 11 cases (18.64%) in group A were markedly effective, 37 cases (62.71%) were effective and 11 cases (18.64%) were ineffective. In group B, 7 cases were markedly effective (11.86%), 37 cases were effective (62.71%) and 15 cases were ineffective (25.42%). In group C, 3 cases were markedly effective (5.17%), 21 cases were effective (36.21%) and 36 cases were ineffective (62.07%). The total effective rate of the traditional Chinese medicine composition group in Embodiment 1 was 81.36%, and there was a statistical difference between the groups (P<0.05), as shown in Table 2.

TABLE 2

Frequency and duration of angina pectoris attacks and evaluation
of curative effect of ST-T segment changes on electrocardiogram

| Group | Case | Markedly effective | Effective | Ineffective | Total effective rate |
|---|---|---|---|---|---|
| Group A | 59 | 11 (18.64%) | 37 (62.71%) | 11 (18.64%) | 81.36% |
| Group B | 59 | 7 (11.86%) | 37 (62.71%) | 15 (25.42%) | 74.58% |
| Group C | 58 | 3 (5.17%) | 21 (36.21%) | 36 (62.07%) | 41.38% |

2.3 Improvement of Left Ventricular Ejection Fraction

After treatment, the ejection fraction of patients in group A increased from 53.68±4.06 to 57.22±3.17%; in group B, the ejection fraction of patients increased from 52.57±2.85% to 55.11±2.33%; in group C, the ejection fraction of patients increased from 52.44±3.91% to 53.60±2.77%, and the ejection fraction of Chinese medicine composition in Embodiment 1 was the most significant, with a statistical difference within the group (P<0.05), as shown in Table 3.

TABLE 3

Improvement of left ventricular ejection fraction (%)

| Group | Case | Before treatment | After treatment |
|---|---|---|---|
| Group A | 59 | 53.68 ± 4.06 | 57.22 ± 3.17* |
| Group B | 59 | 52.57 ± 2.85 | 55.11 ± 2.33* |
| Group C | 58 | 52.44 ± 3.91 | 53.60 ± 2.77* |

Note:
Compared with before treatment *P < 0.05.

2.4 Quality of Life Index Integral Improvement

After treatment, the quality of life index integral of patients in group A increased from 43.12±3.20 to 53.06±2.22; in group B, the quality of life index integral increased from 44.02±2.76 to 48.59±1.51; the quality of life index integral of patients in group C increased from 43.37±2.47 to 46.23±2.35, and the quality of life integral of Chinese medicine composition in Embodiment 1 was the most significant, with a statistical difference within the group (P<0.05), as shown in Table 4.

TABLE 4

Quality of life index integral improvement

| Group | Case | Before treatment | After treatment |
|---|---|---|---|
| Group A | 59 | 43.12 ± 3.20 | 53.06 ± 2.22* |
| Group B | 59 | 44.02 ± 2.76 | 48.59 ± 1.51* |
| Group C | 58 | 43.37 ± 2.47 | 46.23 ± 2.35* |

Note:
Compared with before treatment *P < 0.05.

2.5 Safety Evaluation

No adverse reactions were observed in patients in each group during 8 weeks, blood, urine, and stool routine, as well as liver and kidney function, showed no abnormalities.

What is claimed is:

1. A medicine composition for treating coronary myocardial bridge, wherein the medicine composition comprising the following components in parts by weight: 2-10 parts of scorpion, 2-10 parts of centipede, 15-50 parts of *Radix paeoniae Alba*, 5-25 parts of *Radix glycyrrhizae Preparata*, 10-30 parts of *Rhizoma chuanxiong*, 10-30 parts of *Radix curcumae* and 10-30 parts of *Rhizoma corydalis*.

2. The medicine composition according to claim 1, wherein the medicine composition comprising the following components in parts by weight: 3 parts of scorpion, 2 parts of centipede, 30 parts of *Radix paeoniae Alba*, 10 parts of *Radix glycyrrhizae Preparata*, 15 parts of *Rhizoma chuanxiong*, 15 parts of *Radix curcumae* and 15 parts of *Rhizoma corydalis*.

3. The medicine for treating coronary myocardial bridge, wherein raw materials comprise the medicine composition according to claim 1.

4. The medicine according to claim 3, wherein the medicine also comprises pharmaceutically acceptable excipients.

5. The medicine according to claim 4, wherein the excipients comprise an emulsifier, a filler, a binder, a disintegrant, a colorant and/or a cosolvent.

6. The medicine according to claim 5, wherein a dosage form of the medicine is an oral dosage form.

7. The medicine according to claim 6, wherein the oral dosage form is decoction, granule, capsule, pill, tablet or ointment.

8. A medicine for treating coronary myocardial bridge, wherein raw materials comprise the medicine composition according to claim 2.

9. A preparation method of the medicine according to claim 4, comprising steps of extracting active ingredients in the medicine composition by using a solvent, and then adding the pharmaceutically acceptable excipients to prepare the medicine.

10. A method for treating coronary myocardial bridge in a subject in need thereof comprising administering the medicinal composition according to claim 1 to said subject.

11. A method for treating coronary myocardial bridge in a subject in need thereof comprising administering the medicinal composition according to claim 2 to said subject.

* * * * *